(12) United States Patent
Parks et al.

(10) Patent No.: US 6,395,736 B1
(45) Date of Patent: May 28, 2002

(54) COMPOSITIONS AND METHODS FOR THE TREATMENT OF ANORECTAL DISORDERS

(75) Inventors: Thomas P. Parks, San Mateo; Vivien Mak, Palo Alto; Jung-Chung Lee, Sunnyvale; Charles Lee, Union City, all of CA (US)

(73) Assignee: Cellegy Pharmaceuticals, Inc., So. San Francisco, CA (US)

( * ) Notice: Subject to any disclaimer, the term of this patent is extended or adjusted under 35 U.S.C. 154(b) by 0 days.

(21) Appl. No.: 09/460,306

(22) Filed: Dec. 13, 1999

Related U.S. Application Data

(60) Provisional application No. 60/112,325, filed on Dec. 14, 1998, provisional application No. 60/139,916, filed on Jun. 17, 1999, and provisional application No. 60/155,318, filed on Sep. 21, 1999.

(51) Int. Cl.[7] ............... A61K 31/50; A61K 31/505; A61K 31/44; A61K 31/47; A61K 31/40
(52) U.S. Cl. ............... 514/248; 514/273; 514/353; 514/309; 514/422
(58) Field of Search ............... 514/273, 422, 514/353, 309, 248

(56) References Cited

U.S. PATENT DOCUMENTS

| | | | | |
|---|---|---|---|---|
| 5,234,947 A | * | 8/1993 | Cherksey | 514/449 |
| 5,576,290 A | * | 11/1996 | Hadley | 514/11 |
| 5,693,676 A | * | 12/1997 | Gorfine | 514/742 |
| 5,932,538 A | * | 8/1999 | Garvey et al. | 514/2 |
| 5,948,762 A | * | 9/1999 | Garfield et al. | 514/12 |
| 5,994,294 A | * | 11/1999 | Garvey et al. | 514/2 |

OTHER PUBLICATIONS

Glavind et al Effects of transmural . . . , Abstract, Am. J. Physiol. 1997, vol. 272, pp. G1075–G1082.*
Szilvassy et al., Glibenclamide sensitivity of . . . , Pharmacol. res. 1997, vol. 36/2, pp. 129–133.*
Heyden et al., Response of guinea pig smooth and striated . . . Abstract, Neurourol, Neurourol. Urodyn. 1995, vol. 14/2, pp. 153–168.*
Winquist et al., Glyburide blocks the relaxation . . . , Abstract, J. Pharmacol. Exp. Ther., Abstract 1989, vol. 248/1, pp. 149–156.*
Baird et al., Membrane hyperpolarization . . . , Br. J. Pharmacol. 1990, vol. 100/2, pp. 329–335.*

* cited by examiner

*Primary Examiner*—William R. A. Jarvis
*Assistant Examiner*—Vickie Kim
(74) *Attorney, Agent, or Firm*—Townsend and Townsend and Crew LLP

(57) ABSTRACT

Compositions and methods for the treatment of anorectal disorders are provided in which certain combinations of NO donors, PDE inhibitors, superoxide ($O_2^-$) scavengers, β-adrenergic agonists, cAMP-dependent protein kinase activators, $\alpha_1$-adrenergic antagonists, L-type $Ca^{2+}$ channel blockers, estrogens, ATP-sensitive $K^+$ channel activators and smooth muscle relaxants are used.

4 Claims, 2 Drawing Sheets

COMPOSITIONS AND METHODS FOR THE TREATMENT OF ANORECTAL DISORDERS

CROSS-REFERENCES TO RELATED APPLICATIONS

This application claims priority from U.S. Provisional Applications 60/112,325, filed Dec. 14, 1998; 60/139,916, filed Jun. 17, 1999 and 60/155,318, filed Sep. 21, 1999. The disclosures of each are incorporated herein by reference in their entirety.

STATEMENT AS TO RIGHTS TO INVENTIONS MADE UNDER FEDERALLY SPONSORED RESEARCH AND DEVELOPMENT

Not applicable.

BACKGROUND OF THE INVENTION

This invention is directed to compositions and methods for treating anorectal disorders such as anal fissures, anal ulcer, hemorrhoidal diseases and levator spasm by administering to an appropriate anal area of a subject (for example, the internal anal canal) in need of such treatment an agent or combination of agents which relaxes the internal anal sphincter muscle. More specifically, this invention describes compositions and methods for treating anorectal disorders with agents which induce an increase in cyclic nucleotides in the anal sphincter muscle or mimics the actions of cyclic nucleotides or reduce intracellular calcium concentrations in the affected anal sphincter muscle tissue, thereby reducing anal sphincter hypertonicity and/or spasm in patients afflicted with such disorders.

In general, anal fissure (fissure-in-ano), anal ulcer, hemorrhoidal diseases, and levator spasm (proctalgia fugax) are relatively common benign conditions of the anorectal area which affect subjects, including humans, of all ages, races, and sexes. However, these conditions can be problematical and inconvenient to treat and painful to endure. An anal fissure or ulcer is a tear or ulcer of the mucosa or lining tissue of the distal anal canal. An anal fissure or ulcer can be associated with another systemic or local disease, but is more frequently present as an isolated finding. The typical idiopathic fissure or ulcer is confined to the anal mucosa and usually lies in the posterior midline, distal to the dentate line. An individual with an anal fissure or ulcer frequently experiences anal pain and bleeding, the pain being more pronounced during and after bowel movements.

Hemorrhoids are specialized vascular areas lying subjacent to the anal mucosa. Symptomatic hemorrhoidal diseases are manifested by bleeding, thrombosis and/or prolapse of the hemorrhoidal tissues. Commonly, internal hemorrhoidal tissue bulges into the anal canal during defecation and results in bleeding and pain. As the tissue enlarges, further bleeding, pain, prolapse and thrombosis can ensue. The thrombosis of hemorrhoids is yet another cause of bleeding and pain.

Levator spasm is a condition affecting women more frequently than men. This syndrome is characterized by spasticity of the levator ani muscle, a portion of the anal sphincter complex. The patient suffering from levator spasm may experience severe, episodic rectal pain. A physical exam may reveal spasm of the puborectalis muscle and pain may be reproduced by direct pressure on this muscle. Bleeding is normally not associated with this condition.

Sphincters are circular groups of smooth muscle that control the orifices of hollow organs. Sphincters present throughout the gastrointestinal (GI) tract control the passage of materials through this system of the body. When constricted, the sphincters close orifices leading to the hollow organs, such as the stomach, intestine, anus, etc. In order for the sphincter to open, the muscles must relax. The sphincter that closes the anus (sphincter ani) consists of two sphincter muscle groups. The external anal sphincter is a thin flat plane of striated muscle fibers adherent to the integument surrounding the margin of the anus. The internal anal sphincter (IAS) is a ring of smooth muscle which surrounds the lower extremity of the rectum and is formed by an aggregation of the involuntary smooth muscle fibers. Inflammation locally may cause sphincter spasm and pain.

Anal sphincter spasm is a condition in which the muscles of the internal anal sphincter are under abnormal tension. The strong contractions of the internal anal sphincter associated with sphincter spasm often give rise to painful linear ulcers or crack-like sores, known as rectal fissures, on the margin of the anus, especially after defecation. Anal sphincter spasm is also considered a cause of the pain following rectal surgery or thrombosed hemorrhoids. Current treatments of rectal fissures are directed at relieving sphincter spasm and include dilatation (under anesthesia) or cutting a part of the sphincter (lateral internal sphincterotomy). Applications of heat, cold, witch hazel, topical anesthetics, topical steroids, stool softeners, and bed rest have also been prescribed to treat rectal pain. However, none of these approaches significantly modifies the sphincter spasm itself.

The treatment of, for example, anal fissure has not changed significantly for over 150 years. Typically, non-surgical therapies involving bulk laxatives and/or sitz baths are used. Approximately 60% of the acute anal fissures heal within three weeks under this treatment regimen. Acute anal fissures which do not heal become chronic anal fissures or anal ulcers. The hypertonicity of the internal anal sphincter muscle, which is believed to be the main cause of anal fissures, can be relieved through surgical sphincterotomy. The Standards Task Force of the American Society of Colon and Rectal Surgeons recommends management of chronic anal fissures by "subcutaneous or open lateral internal sphincterotomy, posterior internal sphincterotomy with advanced flap, or manual dilatation". Healing occurs following sphincterotomy in 95% of cases. Successful sphincterotomy (or anal dilatation) is associated with a significant decrease in intra-anal pressure. However, a number of patients experience incontinence following the surgical procedure.

A known moderator of sphincter tone is nitric oxide (NO). Nitric oxide has been shown to bring about a concentration-dependent reduction in the resting tension of internal sphincter smooth muscle strips in vitro (Rattan et al., *Am. J Physiol.* 262:G107–112 (1992)), and NO donors, e.g. nitroglycerin, isosorbide dinitrate, isosorbide mononitrate, reduce anal pressure in man. NO has also been shown to mediate adaptive relaxation of other sphincters in the gastrointestinal tract including the lower esophageal sphincter (Conklin et al., *Gastroenterology* 104:1439–1444 (1993); Tottrup et al., *Br. J Pharmacol.* 104:113–116 (1991)), pyloric sphincter (Bayguinov et al., *Am. J Physiol.* 264:G975–983 (1993), sphincter of Oddi (Mourelle et al., *Gastroenterology* 105:1299–1305 (1993)), and the ileocolic sphincter (Ward et al., *Br. J. Pharmacol.* 105:776–782 (1992)). It is thought that NO or NO-like substances serve as important control mechanisms for the general phenomenon of gastrointestinal adaptive relaxation.

U.S. Pat. Nos. 5,504,117 and 5,693,676 describes the use of NO donors for the treatment of anorectal conditions.

However, the development of adverse side effects such as the development of headaches has limited the use of NO donors in stand alone therapy, especially at higher doses.

There is clearly a significant need for other non-surgical treatments of anorectal disorders, including, for example, anal fissures and other anorectal conditions caused by anal sphincter spasm and or hypertonicity, including acute hemorrhoidal diseases and proctalgia fugax.

SUMMARY OF THE INVENTION

In one aspect, the present invention provides compositions for the treatment of anorectal disorders comprising a nitric oxide donor in combination with a second agent (typically one which modulates levels of cAMP or cGMP). The second agent can be a phosphodiesterase type V (PDE V) inhibitor. a phosphodiesterase type II (PDE II) inhibitor, a phosphodiesterase type IV (PDE IV) inhibitor, a nonspecific PDE inhibitor, a β-adrenergic agonist, a cAMP-dependent protein kinase activator, an estrogen or estogen-like compound, or an $\alpha_1$-adrenergic antagonist. The agent can also be a superoxide anion ($O_2^-$) scavenger, an ATP-sensitive $K^+$ channel activator, or a smooth muscle relaxant, although these agents do not directly modulate either cAMP or cGMP levels. The present invention further provides methods of using these compositions.

In another aspect, the present invention provides compositions for the treatment of anorectal disorders comprising a phosphodiesterase inhibitor, preferably a PDE II inhibitor, a PDE IV inhibitor or a PDE V inhibitor, either alone or in combination with another agent selected from β-adrenergic receptor agonists, $\alpha_1$-adrenergic antagonists, estrogens, L-type $Ca^{2+}$ channel blockers, ATP-sensitive $K^+$ channel activators, or smooth muscle relaxants, in combination with a pharmaceutically acceptable carrier. The present invention also provides methods of using these compositions.

In another aspect, the present invention provides compositions for the treatment of anorectal disorders comprising a β-adrenergic receptor agonist, preferably a $\beta_2$- or $\beta_3$-adrenergic receptor agonist, either alone or in combination with another agent selected from cAMP-hydrolyzing PDE inhibitors (e.g., a PDE IV inhibitor), nonspecific PDE inhibitors, $\alpha_1$-adrenergic antagonists, estrogens or estrogen-like compounds, L-type $Ca^{2+}$ channel blockers, or ATP-sensitive $K^+$ channel activators, and methods of using those compositions.

In yet another aspect, the present invention provides compositions for the treatment of anorectal disorders comprising an ATP-sensitive $K^+$ channel activator, either alone or in combination with another agent selected from cAMP-dependent protein kinase activators, $\alpha_1$-adrenergic antagonists, estrogens, L-type $Ca^{2+}$ channel blockers, or smooth muscle relaxants, and methods of using those compositions.

In still another aspect, the present invention provides compositions for the treatment of anorectal disorders comprising an $\alpha_1$-adrenergic antagonist, either alone or in combination with another agent selected from cAMP-hydrolyzing PDE inhibitors (preferably a PDE IV inhibitor) or smooth muscle relaxants, and methods of using those compositions.

In another aspect, the present invention provides compositions for the treatment of anorectal disorders comprising cyclic nucleotide-dependent protein kinase activators, either alone or in combination with another agent. Methods for the use of these compositions are also provided. In one group of embodiments, cGMP-dependent protein kinase activators are used alone. In another group of embodiments, nonspecific cyclic nucleotide-dependent protein kinase activators are used alone. In yet another group of embodiments, nonspecific cyclic nucleotide-dependent protein kinase activators are used in combination with smooth muscle relaxants. In still another group of embodiments, cAMP-dependent protein kinase activators are provided in combination with L-type $Ca^{2+}$ channel blockers.

In yet another aspect, the present invention provides compositions for the treatment of anorectal disorders comprising an estrogen or other estrogenic compound, either alone or in combination with another agent. Methods for the use of these compositions are also provided. In one group of embodiments, estrogenic compounds are used alone. In another group of embodiments, the estrogenic compounds are used in combination with a second agent selected from phophodiesterase inhibitors, β-adrenergic receptor agonists, $\alpha_1$-adrenergic antagonists, L-type $Ca^{2+}$ channel blockers, ATP-sensitive K+ channel activators, or smooth muscle relaxants, in combination with a pharmaceutically acceptable carrier. The present invention further provides methods of using these compositions.

Methods of treating anorectal disorders are also provided herein. The methods of the invention comprise administering to a subject a suitable formulation of one or more of the compositions above. In related methods, treatment is carried out by administration of two or more agents in sequence, either by the same route of administration or by different routes of administration.

DETAILED DESCRIPTION OF THE INVENTION

Figure 1:
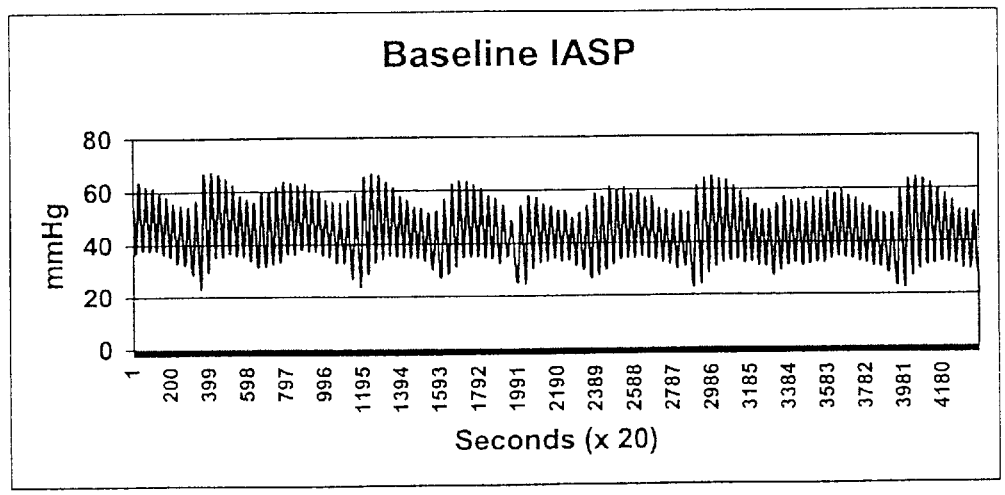
FIG. 1 illustrates a typical waveform pattern for resting IASP in a rat under conditions of a control experiment.

Abbreviations and Definitions cAMP, cyclic adenosine monophosphate; cGMP, cyclic guanosine monophosphate; NO, nitric oxide; NTG, nitroglycerin; SOD, superoxide dismutase; PDE, phosphodiesterase; IASP, internal anal sphincter pressure; Rp-cAMPS, Rp-Adenosine-3',5'-cyclic monophosphorothioate; Sp-cAMPS, Sp-Adenosine-3',5'-cyclic monophosphorothioate; 8-CPT cAMP, 8-(4-Chlorophenylthio)-adenosine-3',5'-cyclic monophosphate, sodium salt; Sp-5,6-DCI-cBiMPS, Sp-5,6-dichloro-1-b-D-ribofuranosylbenzimidazole-3',5'-monophosphorothioate Dibutyryl-cAMP, N6,2'-O-

Dibutyryladenosine-3',5'-cyclic monophosphate, sodium salt monohydrate; Sp-8-pCPT-cGMPS, Sp-8-(4-Chlorophenylthio)-quanosine-3',5'-cyclic monophosphate, sodium salt; 8-Bromo-cGMP, 8-Bromoguanosine-3',5'-cyclic monophosphate, sodium salt; Rp-8-Br-cGMPS, Rp-8-Bromoguanosine-3',5'-cyclic monophosphorothioate, sodium salt; Dibutyryl-cGMP, N2,2'-O-Dibutyrylguanosine-3',5'-cyclic monophosphate, sodium salt; EHNA, erythro-9-(2-Hydroxy-3-nonyl)adenine HCI; IBMX, 3-Isobutyl-1-methylxanthine; MY-5445, 1-(3-Chlorophenylamino)-4-phenylphthalazine; Ro 20-1724, 4-(3-Butoxy-4-methoxybenzyl)-2-imidazolidinone.

Unless defined otherwise, all technical and scientific terms used herein have the same meaning as commonly understood by those of ordinary skill in the art to which this invention belongs. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); and Hale & Marham, THE HARPER COLLINS DICTIONARY OF BIOLOGY (1991). As used herein, the following terms have the meanings ascribed to them unless specified otherwise. Although any methods and materials similar or equivalent to those described herein may be used in the practice or testing of the present invention, the preferred methods and materials are described. For purposes of the present invention, the following terms are defined below.

The terms "treatment", "therapy" and the like include, but are not limited to, changes in the recipient's status. The changes can be either subjective or objective and can relate to features such as symptoms or signs of the disease or condition being treated. For example, if the patient notes decreased itching, reduced bleeding, reduced discomfort or decreased pain, then successful treatment has occurred. Similarly, if the clinician notes objective changes, such as by histological analysis of a biopsy sample, then treatment has also been successful. Alternatively, the clinician may note a decrease in the size of lesions or other abnormalities upon examination of the patient. This would also represent an improvement or a successful treatment. Prevention of deterioration of the recipient's status is also included by the term. Therapeutic benefit includes any of a number of subjective or objective factors indicating a response of the condition being treated as discussed herein.

"Drug", "pharmacological agent", "pharmaceutical agent", "active agent", and "agent" are used interchangeably and are intended to have their broadest interpretation as to any therapeutically active substance which is delivered to a living organism to produce a desired, usually beneficial effect.

"Pharmaceutically-acceptable" or "therapeutically-acceptable" refers to a substance which does not interfere with the effectiveness or the biological activity of the active ingredients and which is not toxic to the hosts, which may be either humans or animals, to which it is administered. "Therapeutically-effective amount" refers to the amount of an active agent sufficient to induce a desired biological result. That result may be alleviation of the signs, symptoms, or causes of a disease, or any other desired alteration of a biological system. The term "therapeutically effective amount" is used herein to denote any amount of the formulation which causes a substantial improvement in a disease condition when applied to the affected areas repeatedly over a period of time. The amount will vary with the condition being treated, the stage of advancement of the condition, and the type and concentration of formulation applied. Appropriate amounts in any given instance will be readily apparent to those skilled in the art or capable of determination by routine experimentation.

The term "anorectal area" is defined herein to include both the anus and the rectum region of a mammal. More particularly, the term includes the internal anal canal, the external anus and the lower rectum.

"Hypertonicity" refers to being in state of greater than normal muscular tension or of incomplete relaxation.

The term "cyclic nucleotide" refers to cyclic adenosine monophosphate and cyclic guanosine monophosphate.

The term "modulation" refers to any systematic variation or graded change in a characteristic (e.g. frequency, concentration, amplitude, effectiveness, etc.) of a sustained oscillation sufficient to affect a biological function. The term "change" includes an increase or decrease in the characteristic.

The term "subject" as used herein includes animal, such as a mammal, including a human.

The term "anorectal disorder" includes any disorder associated with an anal rectal disease, including an acute or chronic anal fissure, an internally or externally thrombosed hemorrhoid, a hemorrhoidal disease, a disorder associated with endoscopic hemorrhoidal ligation or pain caused by such ligation, levator spasm, constipation, and other anorectal disorder caused by hypertonicity or spasm of the anal sphincter muscle. The term "anal fissure" is also referred to as "anal rhagades" and spasms of the anal sphincter are also referred to as "rectal tenesmus." Additionally, the term is meant to include pain which can be associated with any of the above disorders or conditions.

The terms "potassium channel opener" and "potassium channel activator" refer generally to a class of drugs that cause an increased flow of potassium ions from inside an electrically excitable cell to outside the cell via a membrane of the cell which has at least one potassium channel. Potassium channel opener activity may be observed by measuring a hyperpolarization of the cell membrane potential (i.e. a more negative membrane potential) caused by an increase in the flow of potassium ions from inside a cell to outside the cell via a potassium channel in the cell membrane.

The term "pharmaceutical composition" means a composition suitable for pharmaceutical use in a subject, including an animal or human. A pharmaceutical composition generally comprises an effective amount of an active agent and a pharmaceutically acceptable carrier.

The term "pharmaceutically acceptable carrier" encompasses any of the standard pharmaceutical carriers, buffers and excipients, including phosphate-buffered saline solution, water, and emulsions (such as an oil/water or water/oil emulsion), and various types of wetting agents and/or adjuvants. Suitable pharmaceutical carriers and their formulations are described in REMINGTON'S PHARMACEUTICAL SCIENCES (Mack Publishing Co., Easton, 19th ed. 1995). Preferred pharmaceutical carriers depend upon the intended mode of administration of the active agent. Typical modes of administration are described below.

The term "effective amount" means a dosage sufficient to produce a desired result. The desired result may comprise a subjective or objective improvement in the recipient of the dosage.

A "prophylactic treatment" is a treatment administered to a subject who does not exhibit signs of a disease or exhibits only early signs of a disease, wherein treatment is administered for the purpose of decreasing the risk of developing pathology.

A "therapeutic treatment" is a treatment administered to a subject who exhibits signs of pathology, wherein treatment is administered for the purpose of diminishing or eliminating those pathological signs.

The term "appropriate anal area" means any area or tissue of the anus or sphincter that is affected by or subject to anal disorder or disease, including, for example, the external or internal anus, the external or internal anal sphincter, anal sphincter muscle, or external or internal anal canal.

As used herein, the term "NO donor" refers to any organic or inorganic compound that can deliver nitric oxide in a physiologic setting. Also included are those compounds that can be metabolized in vivo into a compound which delivers nitric oxide (e.g., a prodrug form of a NO donor, or a binary NO generating system).

General

A promising new approach for treating anal disorders is the topical application of a nitric oxide (NO) donor to an appropriate anal area. Nitric oxide has been shown to bring about a concentration-dependent reduction in the resting tension of internal sphincter smooth muscle strips in vitro (Rattan et al., *Am. J Physiol.* 262:G107–112 (1992)), and NO donors (e.g., nitroglycerin, isosorbide dinitrate, isosorbide mononitrate, and L-arginine) have been shown to reduce anal pressure in humans. Schouten, W. R. et al., "Pathophysiological aspects and clinical outcome of intra-anal application of isosorbide dinitrate in patients with chronic anal fissure," Gut 39:465–9 (1996); Farid, M., *Br. J Surg.* 84:1 (1997); and Hechtman, H. B. et al., *Arch. Surg.* 131:775–778 (1996). NO has also been shown to mediate adaptive relaxation of other sphincters in the gastrointestinal tract including the lower esophageal sphincter (Conklin et al., *Gastroenterology* 104:1439–1444 (1993); Tottrup et al., *Br. J Pharmacol.* 104:113–116 (1991)), pyloric sphincter (Bayguinov et al., *Am. J Physiol.* 264:G975–983 (1993), sphincter of Oddi (Mourelle et al., *Gastroenterology* 105:1299–1305 (1993)), and the ileocolic sphincter (Ward et al., *Br. J Pharmacol.* 105:776–782 (1992)). It is thought that NO or NO-like substances serve as important control mechanisms for the general phenomenon of gastrointestinal adaptive relaxation.

Despite the initial promise of NO donors, tachyphylaxis has been observed for members of this class of agents. Surprisingly, the present invention provides compositions which are useful to overcome side effects and problems associated with the current therapies.

Description of the Embodiments

NO Donors in Combination with a Second Agent

In one aspect, the present invention provides compositions for the treatment of anal disorders comprising a nitric oxide donor in combination with a second agent which modulates levels of cAMP or cGMP. In one group of embodiments the second agent is a phosphodiesterase type V (PDE V) inhibitor. In another group of embodiments the second agent is a phosphodiesterase type IV (PDE IV) inhibitor. In another group of embodiments the second agent is a phosphodiesterase type II (PDE II) inhibitor. In another group of embodiments the second agent is a nonspecific PDE inhibitor. In still another group of embodiments the second agent is a superoxide anion ($O_2^-$) scavenger. In yet another group of embodiments the second agent is a β-adrenergic agonist. In another group of embodiments, the second agent is a cAMP-dependent protein kinase activator.

In another group of embodiments the second agent is an $α_1$-adrenergic antagonist. In another group of embodiments the second agent is an estrogen, estrogen analog, or estrogenic compound. In another group of embodiments the second agent is an L-type $Ca^{2+}$ channel blocker. In still another group of embodiments the second agent is an ATP-sensitive $K^+$ channel activator. The present invention further provides methods of using the compositions provided above. In a related aspect, the present invention provides compositions comprising an NO donor and a smooth muscle relaxant.

In each of the above embodiments, the nitric oxide donor can be any of a variety of NO donors including, for example, organic NO donors, inorganic NO donors and prodrug forms of NO donors. Preferably, the NO donor includes at least one organic nitrate (including esters of nitric acid) and can be either a cyclic or acyclic compound. For example, suitable NO donors include nitroglycerin (NTG), isosorbide dinitrate (ISDN), isosorbide mononitrate (ISMN) which may include isosorbide-2-mononitrate (IS2N) and/or isosorbide-5-mononitrate (IS5N), erythrityl tetranitrate (ETN), pentaerythrityl tetranitrate (PETN), ethylene glycol dinitrate, isopropyl nitrate, glyceryl-1-mononitrate, glyceryl-1,2-dinitrate, glyceryl-1,3-dinitrate, butane-1,2,4-triol trinitrate, and the like. More preferably, the NO donor is NTG. Nitroglycerin and other organic nitrates including ISDN, ETN, and PETN, have been given regulatory approval for use in treatments in other fields of medicine on human subjects. Additional NO donors include sodium nitroprusside, N,O-diacetyl-N-hydroxy-4-chlorobenzenesulfonamide, $N^G$-hydroxy-L-arginine (NOHA), hydroxyguanidine sulfate, molsidomine, 3-morpholinosydnonimine (SIN-1), (±)-S-nitroso-N-acetylpenicillamine (SNAP), S-nitrosoglutathione (GSNO), (±)-(E)-ethyl-2-[(E)-hydroxyimino]-5-nitro-3-hexeneamide (FK409), (±)-N-[(E)-4-ethyl-3-[(Z)-hydroxyimino]-5-nitro-3-hexen-1-yl]-3-pyridinecarboxamide (FR144420), and 4-hydroxymethyl-3-furoxancarboxamide.

In general, the organic nitric oxide donor, to include the organic nitrate, is present in any amount less than that which is effective in the practice of the treatment of anal disease when used alone. In typical practice of the invention the organic nitric oxide donor can be present in a concentration from about 0.01 to about 10 percent by weight. All weight percentages herein are based on the total weight of the composition. For NTG, preferred concentrations are in the range of from about 0.01 to about 5 percent by weight.

In one group of embodiments, the composition contains an agent which is a phosphodiesterase type V (PDE V) inhibitor. Inhibitors of phosphodiesterases (PDE), are agents which can block the breakdown of cAMP and cGMP in the tissue. PDE inhibitors include both non-specific PDE inhibitors and specific PDE inhibitors (those which inhibit a single type of phosphodiesterase with little, if any, effect on any other type of phosphodiesterase). Phosphodiesterase type V inhibitors include zaprinast, MBCQ, MY-5445, dipyridamole and sildenifil.

In another group of embodiments, the composition contains an agent which is a phosphodiesterase type II (PDE II) inhibitor. Suitable phosphodiesterase type II inhibitors include EHNA.

In yet another group of embodiments, the composition contains an agent which is a phosphodiesterase type IV (PDE IV) inhibitor. Suitable phosphodiesterase type IV inhibitors include ariflo (SB207499), RP73401, CDP840, rolipram and LAS31025.

In yet another group of embodiments, the composition contains an agent which is a nonspecific phosphodiesterase (nonspecific PDE) inhibitor. Suitable nonspecific phosphodiesterase inhibitors include IBMX, theophylline, aminophylline, pentoxifylline, papaverine and caffeine.

In still another group of embodiments, the composition contains an agent which is a superoxide anion ($O_2^-$) scavenger. Superoxide can react with NO and dramatically reduce its biological effects. Accordingly, agents that scavenge superoxide anion (e.g., exogenous Mn- or Cu/Zn superoxide dismutase (SOD) or small molecule SOD mimetics, e.g. Mn(III) tetra(4-benzoic acid) porphyrin chloride (MnTBAP) and M40403, see Salvemini, et al., *Science* 286(5438):304–306 (1999)) can enhance the effects of NO. SODs are relatively stable enzymes and can be used in topical formulations with NO donors such as, for example, NTG, to boost the local potency of NO generated from NTG. The nitric oxide formed from NTG acts only locally due to its short half-life. However, NTG itself is stable enough to exert systemic effects following mucosal absorption. By enhancing the local efficacy of NTG with SOD or a SOD mimetic, less NTG is required to produce the same degree of internal anal sphincter relaxation, and less NTG is absorbed, leading to a reduction in systemic side effects.

In yet another group of embodiments, the composition contains an agent which is a β-adrenergic agonist, preferably a $β_2$- or $β_3$-adrenergic receptor agonist. A variety of β-adrenergic agonists have been described in the literature and are useful in the present invention. Suitable $β_3$-adrenergic agonists are described in, for example, Bristol, et al., ANNUAL REPORTS IN MEDICINAL CHEMISTRY, VOL. 33, Chap. 19, pp 193–202, Academic Press (1998). Preferred β-adrenergic agonists include salbutamol, terbutaline, procaterol, clenbuterol, isoproterenol, zinterol, BRL 37344, CL316243, CGP-12177A, GS 332, L-757793, L-760087, L-764646, and L-766892.

In another group of embodiments, the agent is a cAMP-dependent protein kinase activator. A variety of cyclic nucleotide-dependent protein kinase activators are useful in the present invention including, for example, cAMP mimetics and dual cGMP/cAMP-dependent protein kinase activators. cAMP mimetics are well known to those of skill in the art and include 8-bromo-cAMP, dibutyryl-cAMP, Rp-cAMPS, and Sp-cAMPS. Dual activators include Sp-8-pCPT-cGMPS, Sp-8-bromo-cGMPS and 8-CPT-cAMP.

In yet another group of embodiments, the composition contains an agent which is an estrogen or estrogen analog or mimetic. As used herein, the term "estrogens" is meant to include all forms of estrogen and estrogen-like compounds such as those compounds having estrogen like activity (e.g., those which bind to the estrogen receptor in a competitive binding assay). The estrogens can be either steroidal or nonsteroidal (see, for example, Bristol, et al., ANNUAL REPORTS IN MEDICINAL CHEMISTRY, VOL. 31, Chap. 19, pp 181–190, Academic Press (1996), and references cited therein). Estrogen-like compounds include but are not limited to 17-beta-estrodiol, estrone, mestranol, estradiol valerate, estrodiol dypionate, ethinyl estrodiol, quinestrol, estrone sulfate, phytoestrogens such as falvones, isoflavones (e.g. genistein), resveratrol, coumestan derivatives, other synthetic estrogenic compounds including pesticides (e.g.p, p'-DDT), plasticizers (e.g. bisphenol A), and a variety of other industrial chemicals (e.g. polychlorinated biphenyls).

In yet another group of embodiments, the composition contains an agent which is an $α_1$-adrenergic antagonist. The sympathetic neurotransmitter norepinephrine contracts sphincter smooth muscle via $α_1$-adrenergic receptors. Pharmacological interference with norepinephrine release or binding to $α_1$-adrenergic receptors by administering sympatholytic agents to the appropriate anal area of a subject can also lead to anal sphincter relaxation and improvement of the signs and symptoms of anorectal disorders. Such sympatholytic agents include $α_1$-adrenergic receptor antagonists (e.g. prazosin, doxazosin, phentolamine, tolazoline, and the like as described in Goodman & Gilman's THE PHARMACOLOGICAL BASIS OF THERAPEUTICS, ninth edition, ed. J G Hardman, et al., McGraw-Hill 1996), $α_2$-adrenergic agonists which block norepinephrine release (e.g. clonidine), nerve terminal norepinephrine depleting agents (e.g. guanethidine, bretylium, reserpine), norepinephrine synthesis inhibitors (e.g. α-methyl tyrosine), and agents which destroy sympathetic nerve terminals (e.g. 6-hydroxy dopamine). Accordingly, in a related embodiment, the composition contains an alternative sympatholytic agent, such as an $α_2$-adrenergic receptor agonist, a nerve terminal norepinephrine depleting agent, a norepinephrine synthesis inhibitor or another agent which destroys sympathetic nerve terminals.

In still another group of embodiments the agent is an ATP-sensitive $K^+$ channel activator. ATP, along with NO, is thought to serve as an inhibitory neurotransmitter released from the enteric non-adrenergic, non-cholinergic nerves that mediate adaptive relaxation of gastrointestinal smooth muscle (Burnstock, *Pharmacol. Rev.* 24:509–81 (1972)). ATP appears to act primarily by opening ATP-sensitive potassium ($K_{ATP}$) channels which hyperpolarize the cell membrane, reducing intracellular calcium concentrations, leading to smooth muscle relaxation. Synthetic compounds that activate ATP-sensitive $K^+$ channels are smooth muscle relaxants, e.g. minoxidil, minoxidil sulfate, pinacidil, diazoxide, levcromakalim, cromakalim, etc. (see, White, et al. *Eur. J Pharmacol.* 357(1):41–51 (1998)). ATP-sensitive potassium channels are expressed by GI smooth muscle (see, Koh, et al. *Biophys. J.* 75:1793–80 (1998)). Accordingly, specific potassium channel openers will be useful for relaxing internal anal sphincter smooth muscle and improving the signs and symptoms of anorectal disorders. It should be noted that other $K^+$ channels can also influence smooth muscle tone, including apamin-sensitive low conductance calcium-activated $K^+$ channels and charybdotoxin-sensitive high conductance calcium-activated $K^+$ channels.

In still other embodiments, the compositions will comprise NO donors and smooth muscle relaxants. Preferred smooth muscle relaxants include, for example, hydralazine, papaverine, tiropramide, cyclandelate, isoxsuprine or nylidrin.

Phosphodiesterase Inhibitor Compositions

In another aspect, the present invention provides compositions for the treatment of anorectal disorders comprising a phosphodiesterase inhibitor, preferably a PDE II inhibitor, a PDE IV inhibitor or a PDE V inhibitor, either alone or in combination with another agent selected from β-adrenergic receptor agonists, $α_1$-adrenergic antagonists, estrogens, L-type $Ca^{2+}$ channel blockers, ATP-sensitive $K^+$ channel activators, or smooth muscle relaxants, in combination with a pharmaceutically acceptable carrier. The present invention also provides methods of using these compositions.

Phosphodiesterase inhibitors (PDE inhibitors) are agents which can block the breakdown of cAMP and cGMP in the tissue. PDE inhibitors include non-specific PDE inhibitors and specific PDE inhibitors. A non-specific PDE inhibitor inhibits more than one type of phosphodiesterase, while a specific PDE inhibitor inhibits only one type of phosphodiesterase with little, if any, effect on any other type of phosphodiesterase. Specific inhibitors of five cyclic nucleotide PDE isozyme families have been characterized:

8-methoxymethyl-IBMX (isobutyl methylxanthine) or vinpocetine ($Ca^{2+}$, calmodulin-dependent PDE type I); EHNA (erythro-9-(2-hydroxy-3-nonyl)adenine HCl) (cGMP-stimulated PDE type II); milrinone (cGMP-inhibited PDE type III); rolipram (cAMP-specific PDE type IV); and zaprinast and DMPPO (1,3 dimethyl-6-(2-propoxy-5 methane sulphonylamidophenyl)-pyrazolo[3,4-d]pyrimidin-4-(5H)-one) (cGMP-specific PDE type V). Current knowledge suggests that there are at least nine classes of PDE isozymes with type 9A having been recently discovered (see, Fisher, et al., *J Biol. Chem.* 273(25):15559–15564 (1998)). Agents which are non-specific inhibitors of PDEs include, for example, IBMX, theophylline, aminophylline, caffeine, etc. (see, Vemulapalli, et al., *J Cardiovasc. Pharmacol.* 28(6):862–9 (1996)).

Preferably, the compositions for treating anorectal disorders contain one or more compounds selected from the classes of PDE II, PDE IV and PDE V inhibitors, in a formulation suitable for local treatment. Members of each of these classes can be advantageously combined with a second agent selected from the group of β-adrenergic receptor agonists, preferably a $β_2$- or $β_3$-adrenergic receptor agonists, $α_1$-adrenergic antagonists, L-type $Ca^{2+}$ channel blockers, estrogens, ATP-sensitive $K^+$ channel activators, or smooth muscle relaxants. Preferred members from each class of additional agent are those which have been described above for use with NO donors.

β-adrenergic Receptor Agonist Compositions

In another aspect, the present invention provides pharmaceutical compositions for the treatment of anorectal disorders comprising a βadrenergic receptor agonist, preferably a $β_2$- or $β_3$-adrenergic receptor agonist, either alone or in combination with another agent selected from cAMP-hydrolyzing PDE inhibitors (e.g., a PDE IV inhibitor), nonspecific PDE inhibitors, $α_1$-adrenergic antagonists, estrogens, L-type $Ca^{2+}$ channel blockers, ATP-sensitive $K^+$ channel activators, or smooth muscle relaxants, and a pharmaceutically acceptable carrier. The present invention further provides methods of using those compositions.

In this aspect of the invention, the β-adrenergic receptor agonist can be essentially any of the β-adrenergic receptor agonists provided above for use in combination with NO donors. Preferably, the βadrenergic agonist, is a $β_2$- or $β_3$-adrenergic receptor agonist. Particularly preferred β-adrenergic agonists are those described in Bristol, et al., ANNUAL REPORTS IN MEDICINAL CHEMISTRY, VOL. 33, Chap. 19, pp 193–202, Academic Press (1998) or are selected from salbutamol, terbutaline, procaterol, clenbuterol, isoproterenol, zinterol, BRL 37344, CL316243, CGP-12177A, GS 332, L-757793, L-760087, L-764646, and L-766892.

In one group of embodiments, the composition contains a suitable β-adrenergic receptor agonist and a pharmaceutically acceptable carrier, preferably one formulated for local delivery to the site of the anorectal disease or disorder.

In another group of embodiments, the composition contains another agent selected from cAMP-hydrolyzing PDE inhibitors (e.g., a PDE IV inhibitor), nonspecific PDE inhibitors, $α_1$-adrenergic antagonists, estrogens, L-type $Ca^{2+}$ channel blockers, ATP-sensitive $K^+$ channel activators or smooth muscle relaxants.

In one preferred group of embodiments, the agent is a cAMP-hydrolyzing PDE inhibitor, more preferably a phosphodiesterase type IV inhibitor. Preferred phosphodiesterase type IV (also referred to as PDE IV and PDE4) inhibitors are described in, for example, Bristol, et al., ANNUAL REPORTS IN MEDICINAL CHEMISTRY, VOL. 33, Chap. 10, pp 91–109, Academic Press (1998). Most preferably, the PDE IV inhibitor is rolipram, Ro 20-1724 or Etazolate.

In another group of preferred embodiments, the agent is a nonspecific PDE inhibitor such as, for example, IBMX, aminophylline, theophylline, pentoxifylline, lisophylline and papaverine.

In yet another group of preferred embodiments, the agent is an $α_1$-adrenergic antagonist. Suitable $α_1$-adrenergic receptor antagonists (e.g. prazosin, doxazosin, phentolamine, tolazoline, and the like) are described in Goodman & Gilman's THE PHARMACOLOGICAL BASIS OF THERAPEUTICS, ninth edition, ed. J G Hardman, et al., McGraw-Hill (1996). Preferred agents for use in these compositions are selected from prazosin, doxazosin, phentolamine, tolazoline and their derivatives.

In still other preferred embodiments, the β-adrenergic receptor agonist is combined with an L-type $Ca^{2+}$ channel blocker, such as, for example, nifedipine, nimodipine, felopidine, nicardipine, isradipine, amlodipine, diltiazem and verapamil.

In yet other preferred embodiments, the β-adrenergic receptor agonist is combined with an ATP-sensitive $K^+$ channel activator. Preferred agents within this group are the same as those that have been provided above for use with NO donors.

Additional compositions are those in which a β-adrenergic receptor agonist is combined with an estrogen or estrogen like compound, or with a smooth muscle relaxant. Suitable compounds within each of these classes have been described above for use with NO donors.

Potassium Channel Activator Compositions

In yet another aspect, the present invention provides compositions for the treatment of anorectal disorders comprising an ATP-sensitive $K^+$ channel activator, either alone or in combination with another agent selected from cAMP-dependent protein kinase activators, estrogens, $α_1$-adrenergic antagonists, L-type $Ca^{2+}$ channel blockers, or smooth muscle relaxants, and a pharmaceutically acceptable carrier. The present invention further provides methods of using those compositions.

In this aspect of the invention, the selected combinations are made from the components described in detail above for the NO donor compositions. Additional description of ATP-sensitive potassium ion channel activators can be found in, for example, Bristol, et al., ANNUAL REPORTS IN MEDICINAL CHEMISTRY, VOL. 29, Chap. 8, pp 73–82, Academic Press (1991). In preferred embodiments the potassium ion channel activator is diazoxide, minoxidil, PCO 400, pinacidil, levcromakalim, or cromokalim.

In some embodiments, the composition comprises an additional agent which is a cAMP-dependent protein kinase activator, an estrogen or estrogen like compound, an $α_1$-adrenergic antagonist, an L-type $Ca^{2+}$ channel blocker, or a smooth muscle relaxant. Preferably, the cAMP-dependent protein kinase activator is a cAMP mimetic or a dual cGMP/cAMP-dependent protein kinase activator. More preferably, the cAMP mimetic is 8-bromo-cAMP, dibutyryl-cAMP, Rp-cAMPS, or Sp-cAMPS, and the dual activator is selected from Sp-8-pCPT-cGMPS, Sp-8-bromo-cGMPS and 8-CPT-cAMP.

In one group of embodiments, an $α_1$-adrenergic antagonist is combined with an ATP-sensitive potassium ion channel activator. Preferably, the $α_1$-adrenergic antagonist is prazosin, phentolamine or tolazoline.

In another group of embodiments, an L-type $Ca^{2+}$ channel blocker is combined with an ATP-sensitive potassium ion channel activator. Preferably, the L-type $Ca^{2+}$ channel blocker is nifedipine, nimodipine, felopidine, nicardipine, isradipine, amlodipine, diltiazem or verapamil.

In still another group of embodiments, a smooth muscle relaxant is combined with an ATP-sensitive potassium ion channel activator. Preferably, the smooth muscle relaxant is hydralazine, papaverine, tiropramide, cyclandelate, isoxsuprine or nylidrin.

$\alpha_1$-Adrenergic Antagonist Compositions

In still another aspect, the present invention provides compositions for the treatment of anorectal disorders comprising an $\alpha_1$-adrenergic antagonist, either alone or in combination with another agent selected from cAMP-hydrolyzing PDE inhibitors (preferably a PDE IV inhibitor), estrogens or smooth muscle relaxants, and a pharmaceutically acceptable carrier. The present invention further provides methods of using those compositions.

$\alpha_1$-Adrenergic antagonists which are useful in this aspect of the invention have been described above and can be found in, for example, Goodman & Gilman's THE PHARMACOLOGICAL BASIS OF THERAPEUTICS, ninth edition, ed. J G Hardman, et al., McGraw-Hill (1996). Preferred $\alpha_1$-adrenergic antagonists are prazosin, phentolamine and tolazoline.

For those embodiments in which an $\alpha_1$-adrenergic antagonist is combined with a cAMP-hydrolyzing PDE inhibitor (preferably a PDE IV inhibitor), an estrogen or estrogen like compound or smooth muscle relaxant, the preferred members of each class are those which have been described above for use with NO donors.

Cyclic Nucleotide-dependent Protein Kinase Activator Compositions

In another aspect, the present invention provides pharmaceutical compositions for the treatment of anorectal disorders comprising cyclic nucleotide-dependent protein kinase activators, either alone or in combination with another agent. Methods for the use of these compositions are also provided. In one group of embodiments, cGMP-dependent protein kinase activators are used alone. In another group of embodiments, nonspecific cyclic nucleotide-dependent protein kinase activators are used alone. In yet another group of embodiments, nonspecific cyclic nucleotide-dependent protein kinase activators are used in combination with smooth muscle relaxants. In still another group of embodiments, cAMP-dependent protein kinase activators are provided in combination with L-type $Ca^{2+}$ channel blockers.

In each instance, preferred members of the recited classes of compounds are those that have been described above for use alone or in other combinations.

Estrogen and Estrogen Mimetic Compositions

In another aspect, the present invention provides pharmaceutical compositions for the treatment of anorectal disorders comprising estrogen or an estrogen mimetic, either alone or in combination with another agent from any of the classes of agents described above. Estrogen-like compounds include but not limited to 17-beta-estrodiol, estrone, mestranol, estradiol valerate, estrodiol dypionate, ethinyl estrodil, quinestrol, estrone sulfate, phytoestrogens such as falvones, isoflavones (e.g. genistein), resveratrol, coumestan derivatives, other synthetic estrogenic compounds including pesticides (e.g.p,p'-DDT), plasticizers (e.g. bisphenol A), and a varietey of other industrial chemicals (e.g. polychlorinated biphenyls) (Goodman & Gilman's THE PHARMACOLOGICAL BASIS OF THERAPEUTICS, ninth edition, ed. J G Hardman, et al., McGraw-Hill (1996). Preferred agents are selected from those described with reference to the compositions of single agents or combinations above. Methods for the use of these compositions are also provided.

Formulations for the Treatment of Anorectal Disorders

Many of the individual components of the compositions above have been described for use in a variety of disease states. However, certain classes and combinations of classes have now been found to be useful for the treatment of anorectal diseases and can be provided in formulations best suited for delivery to an appropriate anal area. Preferred formulations are those in which the components are combined in a topical formulation for local application to the external or internal anus, the external or internal anal sphincter, anal sphincter muscle, the external or internal anal canal and the lower rectum above the anal canal.

Accordingly, each of the compositions provided above will typically be presented in an appropriate pharmaceutical formulation comprising an effective amount of the noted agents (e.g., NO donors, $\beta_2$- or $\beta_3$-adrenergic receptor agonists, cAMP-hydrolyzing PDE inhibitors, nonspecific PDE inhibitors, $\alpha_1$-adrenergic antagonists, L-type $Ca^{2+}$ channel blockers, ATP-sensitive $K^+$ channel activators, and the like).

One of skill in the art will appreciate that suitable formulations are dependent on the form of delivery to be employed, and all such forms are contemplated by the present invention. Additionally, in some embodiments, combinations of agents are employed in a single formulation, while in other embodiments, agents are formulated separately, but administered in combination, or sequentially. In the discussion below, compositions of single agents will be understood to also include compositions of two or more agents. Still further, different formulations can be used for those embodiments in which agents are administered separately or sequentially, by different routes of administration.

Topical Compositions

In view of the above, the present invention provides topical compositions useful for treating anorectal disorders (including those related to hypertonicity and/or spasm of the internal anal sphincter muscle, e.g. hemorrhoidal pain) and for treating spasms of the mammal, including humans, which comprise an effective amount of an agent that prevents the contraction of anal sphincter muscle and a pharmaceutically acceptable carrier. In one embodiment, the agent is an ATP-sensitive potassium channel opener. In another embodiment, the agent is a phosphodiesterase inhibitor, a cyclic nucleotide mimic, $\beta$-adrenergic agonist, an estrogen or estrogen like compound, an $\alpha_1$-adrenergic antagonist.

In related embodiments, the present invention provides topical pharmaceutical compositions in unit dosage form comprising per unit dosage an amount of the agent or combination provided above, which is effective for treating an anal disorder in a subject in need of such treatment. Typically the agents are in combination with a pharmaceutically acceptable carrier. Such compositions are useful in treating or reducing pain associated with anal disorders, such as hemorrhoidal pain, and for treating spasms and/or hypertonicity of the sphincters, including the internal anal sphincter, lower esophageal sphincter, pyloric sphincter, sphincter of Oddi, and the ileocolic sphincter. The topical composition is also useful in treating conditions resulting from spasms and/or hypertonicity of sphincters of the anorectal region including anal fissure, post-operative rectal pain, hypertrophic pyloric stenosis, and pancreatitis, as well as conditions resulting from general spasm of the muscles of the GI tract including Zenkers diverticulum, achalasia, esophageal spasm (nutcracker esophagus), irritable bowel disease, and Hirshprungs disease (bowel obstruction). In addition, the topical compositions are useful for relaxing the anal sphincter and reducing pain before, during and after examinations of the anus, rectum and lower gastointestinal system, insertion of instruments and procedures, such as surgery.

Dosage Forms

Dosage forms for the topical administration of the anal sphincter relaxing agents of this invention include powders, sprays, ointments, pastes, creams, lotions, gels, solutions, patches, suppositories and liposomal preparations. The dosage forms may be formulated with mucoadhesive polymers for sustained release of actives at the anal mucosa. The active compound may be mixed under sterile conditions with a pharmaceutically acceptable carrier, and with any preservatives, buffers, or propellants, which may be required. Topical preparations can be prepared by combining the anal sphincter relaxing agent with conventional pharmaceutical diluents and carriers commonly used in topical dry, liquid, cream and aerosol formulations. Ointment and creams may, for example, be formulated with an aqueous or oily base with the addition of suitable thickening and/or gelling agents. Such bases may include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, and the like. Lotions may be formulated with an aqueous or oily base and, in general, also include one or more of the following: stabilizing agents, emulsifying agents, dispersing agents, suspending agents, thickening agents, coloring agents, perfumes, and the like. Powders may be formed with the aid of any suitable powder base, e.g., talc, lactose, starch, and the like. Drops may be formulated with an aqueous base or non-aqueous base also comprising one or more dispersing agents, suspending agents, solubilizing agents, and the like.

The ointments, pastes, creams and gels also may contain excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays also can contain excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Representative compositions include topical compositions comprising one or more of the following first pharmacologic agents: an NO donor, phosphodiesterase inhibitor, cyclic nucleotide mimetic, β-adrenergic agonist, L-type calcium channel blocker, α-adrenergic antagonist, ATP-sensitive potassium channel activator, estrogen or estrogen-like compound or botulinum toxin in combination with a pharmaceutically acceptable carrier and at least one of the following second pharmacologic agents: a local anesthetic (e.g., lidocaine, prilocaine, etc.), local anti-inflammatory agent (e.g., naproxen, pramoxicam, etc.), corticosteroid (e.g., cortisone, hydrocortisone, etc.), anti-itch agent (e.g., loperamide diphylenoxalate, etc.), an agent that interferes with the activation of peripheral sensory neurons, including divalent and trivalent metal ions (e.g., manganese, calcium, strontium, nickel, lanthanum, cerium, zinc, etc.), analgesic agents, yeast-based product (e.g., lyophilized yeast, yeast extract, etc.), growth-promoting and/or wound healing-promoting agent known to promote re-epithelialization (e.g., platelet-derived growth factor PDGF, interleukin-11 (IL-11) etc.), anti-microbial agent (e.g., neosporin, polymyxin B sulfate, bacitracin zinc, etc.), mucoadhesive agent (e.g., cellulose derivatives, etc.), cytoprotectant agent (e.g., colloidal bismuth, misoprostol, etc., with the exception of sucralfate) as defined in GOODMAN & GILMAN'S THE PHARMACOLOGICAL BASIS OF THERAPEUTICS, supra, an agent that promotes local tissue sclerosis (e.g., alum, etc.), or menthol. The at least one first pharmacologic agent is typically present in the composition in unit dosage form effective treatment for a first medical condition(s), such as an anal disease or pain associated. The at least one second pharmacologic agent is typically present in the composition in unit dosage form effective for treatment of a second medical condition(s), or a condition(s), symptom(s) or effect(s) associated with or resulting from the first medical condition(s).

In one aspect, the invention provides compositions for treating anorectal disorders which comprise an active agent and a pharmaceutically acceptable carrier. The active agent comprises an agent that stimulates or causes an increase of either cGMP or cAMP through activation of guanylyl or adenylyl cyclase, respectively, a cyclic nucleotide mimetic, PDE inhibitor, a-adrenergic receptor antagonist, or β-adrenergic receptor agonist, or potassium channel opener. In one aspect, the active agent is present in compositions of the invention in an amount of from about 0.001% to about 15% by weight of the composition. In another aspect, the active agent is present in an amount of from about 0.01% to about 7.5% by weight or from about 0.05% to about 2% by weight of the composition.

For example, in one group of embodiments, the invention provides compositions for treating anorectal disorders comprising a pharmaceutically acceptable carrier and an amount of from about 0.001% to about 15% sildenafil by weight. In another aspect, compositions comprising a pharmaceutically acceptable carrier and an amount of from about 0.01% to about 7.5% or from about 0.05% to about 2% sildenafil by weight are provided.

The topical pharmaceutical compositions can also include one or more preservatives or bacteriostatic agents, e.g., methyl hydroxybenzoate, propyl hydroxybenzoate, chlorocresol, benzalkonium chlorides, and the like. The topical pharmaceutical compositions also can contain other active ingredients such as antimicrobial agents, particularly antibiotics, anesthetics, analgesics, and antipruritic agents.

One example of a topical formulation includes 75% (w/w) white petrolatum USP, 4% (w/w) paraffin wax USP/NF, lanolin 14% (w/w), 2% sorbitan sesquioleate NF, 4% propylene glycol USP, and 1% anal sphincter relaxing agent.

The dosage of a specific anal sphincter relaxing agent depends upon many factors that are well known to those skilled in the art, for example, the particular agent; the condition being treated; the age, weight, and clinical condition of the recipient patient; and the experience and judgment of the clinician or practitioner administering the therapy. An effective amount of the compound is that which provides either subjective relief of symptoms or an objectively identifiable improvement as noted by the clinician or other qualified observer. The dosing range varies with the compound used, the route of administration and the potency of the particular compound.

Transmucosal (i.e., sublingual, rectal, colonic, pulmonary, buccal and vaginal) drug delivery provides for an efficient entry of active substances to systemic circulation and reduces immediate metabolism by the liver and intestinal wall flora (See Chien Y. W., NOVEL DRUG DELIVERY SYSTEMS, Chapter 4 "Mucosal Drug Delivery," Marcel Dekker, Inc. (992). Transmucosal drug dosage forms (e.g., tablet, suppository, ointment, gel, pessary, membrane, and powder) are typically held in contact with the mucosal membrane and disintegrate and/or dissolve rapidly to allow immediate local and systemic absorption. These formulations are used along with the anti-inflammatory agents of the present invention for reducing or eliminating inflammation of transmucosal membranes.

Sustained or Controlled Delivery Formulations

In yet other embodiments, the invention provides topical sustained and prolonged release pharmaceutical compositions comprising one or more anal sphincter relaxant, including nitric oxide donors (such as nitroglycerin, isosorbide dinitrate, and L-arginine) or the pharmacological agents described above and a pharmaceutically acceptable carrier, to treat anorectal disorders. Such compositions are useful in the treatment of such disorders and in controlling and reducing pain associated with such disorders. Such compositions may comprise a unit dosage of one or more particular active agent (e.g., nitric oxide donor) which is effective in treating anal disorders and in controlling and alleviating pain associated therewith. Preferably, the compositions are administered in unit dosage form to a subject in need of such treatment. In other embodiments, the compositions contain an NO donor in an amount which is less than an effective amount when used alone, but which is effective when used in combination with a second agent which modulates levels of cAMP or cGMP in a subject. Topical sustained and prolonged release compositions are typically variants which include 1) an absorbent in a hydrophilic base; 2) an absorbent in a hydrophobic base; and 3) coated beads containing an absorbent matrix dispersed in a suitable vehicle. Also provided are methods of treating anal or GI tract disorders comprising topically administering an effective amount of such compositions (e.g., in unit dosage form) to the appropriate anal area of the subject in need of such treatment.

Such hydrophilic compositions and preparations of the invention comprise a nitric oxide donor (or other suitable agent or combination of agents) and a polymer, such as cellulose (methyl cellulose, ethyl cellulose, hydroxy propyl cellulose, etc.), higher molecular weight polyethylene glycol, methacrylic-acrylic acid emulsion, hydrogel, carbopol, ethyl vinyl acetate copolymer, or polyester, etc., to bind the nitric oxide donor to the polymer. The nitric oxide donor-polymer matrix or agent-polymer matrix is then dispersed in a hydrophilic vehicle to form a semi-solid. After administration of such hydrophilic composition into the appropriate anal area, such as the anal canal or anal sphincter, the water in the semi-solid preparation is adsorbed and the polymer matrix with the active ingredient—the nitric oxide donor or other agent—remains as a coating in the anal region or area to which it has been applied. The nitric oxide donor is then slowly released from this coating.

Hydrophobic compositions and preparations of the inventions employ similar polymers as used in the hydrophilic preparations, but the polymer/nitric oxide donor matrix is dispersed into a vehicle, such a plastibase, in the hydrophobic compositions and preparations. Plastibase is a mineral oil base that only partially dissolves the nitric oxide donor. The semi-solid composition forms a thin coating on the anal region to which the composition has been applied (such as the anal canal or anal sphincter area) and slowly releases the active. The prolonged action is controlled principally by the solubility of the active ingredient (nitric oxide donor) in the vehicle.

The present invention also provides coated beads which are produced by first absorbing the nitric oxide donor or other agent or combination of agents on a cellulosic material blended with polyethylene glycol, filler, binder and other excipients. The resulting matrix is then extruded and spheronized (e.g., the process of making into spheres) to create small beads. The beads are then coated to an appropriate thickness with one or more of a suitable material, such as a methacrylic-acrylic polymer, polyurethane, ethyl vinyl acetate copolymer, polyester, silastic, etc. The coating on the beads acts as a rate controlling membrane which regulates the release of the agent from the core beads.

Oral Formulations

In still another embodiment, the invention provides pharmaceutical compositions suitable for oral administration which are provided in unit dosage form comprising per unit dosage a phosphodiesterase inhibitor, cyclic nucleotide mimetic, or βadrenergic agonist, and a pharmaceutically acceptable carrier. Such compositions are useful for treating anorectal disorders, including those disorders and conditions provided above.

For delivery to the buccal membranes, typically an oral formulation, such as a lozenge, tablet, or capsule is used. The method of manufacture of these formulations are known in the art, including but not limited to, the addition of a pharmacological agent to a pre-manufactured tablet; cold compression of an inert filler, a binder, and either a pharmacological agent or a substance containing the agent (as described in U.S. Pat. No. 4,806,356); and encapsulation. Another oral formulation is one that can be applied with an adhesive, such as the cellulose derivative, hydroxypropyl cellulose, to the oral mucosa, for example as described in U.S. Pat. No. 4,940,587. This buccal adhesive formulation, when applied to the buccal mucosa, allows for controlled release of the pharmacological agent into the mouth and through the buccal mucosa. The anti-inflammatory agents of the present invention can be incorporated into these formulations as well.

Aerosol Formulations

For delivery to the nasal or bronchial membranes, typically an aerosol formulation is employed. The term "aerosol" includes any gas-borne suspended phase of the pharmacological agent which is capable of being inhaled into the bronchioles or nasal passages. Specifically, aerosol includes a gas-borne suspension of droplets of the compounds of the instant invention, as may be produced in a metered dose inhaler or nebulizer, or in a mist sprayer. Aerosol also includes a dry powder composition of a compound of the pharmacological agent suspended in air or other carrier gas, which may be delivered by insufflation from an inhaler device, for example. For solutions used in making aerosols, the preferred range of concentration of the pharmacological agent is 0.1–100 milligrams (mg)/ milliliter (mL), more preferably 0.1–30 mg/mL, and most preferably, –10 mg/mL. Usually the solutions are buffered with a physiologically compatible buffer such as phosphate or bicarbonate. The usual pH range is 5 to 9, preferably 6.5 to 7.8, and more preferably 7.0 to 7.6. Typically, sodium chloride is added to adjust the osmolarity to the physiological range, preferably within 10% of isotonic. Formulation of such solutions for creating aerosol inhalants is discussed in Remington's 5 Pharmaceutical Sciences, see also, Ganderton and Jones, DRUG DELIVERY TO THE RESPIRATORY TRACT, Ellis Horwood (1987); Gonda (1990) *Critical Reviews in Therapeutic Drug Carrier Systems* 6:273–313; and Raeburn et al. (1992) *J Pharmacol. Toxicol. Methods* 27:143–159.

Solutions of the pharmacological agent may be converted into aerosols by any of the known means routinely used for making aerosol inhalant pharmaceuticals. In general, such methods comprise pressurizing or providing a means of pressurizing a container of the solution, usually with an inert carrier gas, and passing the pressurized gas through a small orifice, thereby pulling droplets of the solution into the mouth and trachea of the animal to which the drug is to be administered. Typically, a mouthpiece is fitted to the outlet of the orifice to facilitate delivery into the mouth and trachea.

Parenteral Formulations

In yet another embodiment, the invention provides pharmaceutical compositions suitable for parental administration which are provided in unit dosage form comprising per unit dosage a phosphodiesterase inhibitor, cyclic nucleotide mimetic, or βadrenergic agonist, and a pharmaceutically acceptable carrier. Such compositions are useful for treating anorectal disorders and conditions as described above.

Topical Systemic Formulations

Solutions and aqueous suspensions are the pharmaceutical forms most widely used to administer drugs that must be active on the eye surface or in the eye after passage through the cornea or conjunctiva. To increase bioavailability of drugs, to extend therapeutic efficacy, and to improve patient compliance, various dosage forms have been developed over the years. These include soluble inserts (undergoing gradual dissolution/or surface erosion), insoluble inserts (e.g., medicated contact lenses such as Ocusert®, etc.), gels (e.g., Gelrite®, liposomal and drug delivery via nanoparticles (emulsion, suspension, etc.), and ointment (See Edman, BIOPHARMACEUTICS OF OCULAR DRUG DELIVERY, CRC Press, 1993).

Methods of Treating Anorectal Disorders

In another aspect, the present invention provides methods for treating anorectal disorders which comprises administering to an appropriate anal area or affected anal tissue (e.g., external or internal anal tissue or anal canal) of a subject in need of such treatment an effective amount of any of the compositions provided above. By use of such methods of the invention, anorectal hypertonicity and/or spasms are relieved and signs and symptoms associated with anorectal disorders, e.g. anal fissures, anal ulcers and hemorrhoids, and pain are improved. The methods described herein are also applicable to the treatment of recurrent anal diseases, and are also useful for relaxing the anal sphincter and reducing pain during anorectal exams (in patients with and without disorders), particularly during procedures when instruments are inserted into the anus.

The present invention further provides methods of using the compositions above in combination with local anesthetic agents, for example lidocaine, prilocaine, etc. Each of the compositions will typically be in a pharmaceutically acceptable dosage form as an effective treatment for a medical condition such as hemorrhoidal pain and for treating spasms and/or hypertonicity of the sphincters including the internal anal sphincter, lower esophageal sphincter, pyloric sphincter, sphincter of Oddi, and the ileocolic sphincter. These pharmaceutical preparations are also useful in treating conditions resulting from spasms and/or hypertonicity of sphincters of the anorectal region including anal fissure, post-operative rectal pain, hypertrophic pyloric stenosis, and pancreatitis, as well as conditions resulting from general spasm of the muscles of the GI tract including Zenkers diverticulum, achalasia, esophageal spasm (nutcracker esophagus), irritable bowel disease, and Hirschsprung's disease (bowel obstruction). In another aspect, the present invention provides methods for treating anal disorders which comprise administering an effective amount of such composition along with a local anesthetic agent to a subject in need of such treatment. Such compositions can be administered orally, topically, or parenterally.

Similarly, the invention provides methods of using the compositions above in combinations with local anti-inflammatory agents, for example, naproxen, piroxicam, etc. in a pharmaceutically acceptable dosage form as an effective treatment for a medical condition such as hemorrhoidal pain and for treating hypertonicity and/or spasms of the sphincters including the internal anal sphincter, lower esophageal sphincter, pyloric sphincter, sphincter of Oddi, and the ileocolic sphincter. These pharmaceutical preparations are also useful in treating conditions resulting from spasms and/or hypertonicity of sphincters of the anorectal region including anal fissure, post-operative rectal pain, hypertrophic pyloric stenosis, and pancreatitis, as well as conditions resulting from general spasm of the muscles of the GI tract including Zenkers diverticulum, achalasia, esophageal spasm (nutcracker esophagus), irritable bowel disease, and Hirschsprung's disease (bowel obstruction). In another aspect, the present invention provides methods for treating anal disorders which comprise administering an effective amount of such composition along with a local anesthetic agent to a subject in need of such treatment. Such compositions can be administered orally, topically, or parenterally.

Additional methods provided by the present invention are those in which two or more agents selected from NO donors, phosphodiesterase type V (PDE V) inhibitor. a phosphodiesterase type II (PDE II) inhibitor, a nonspecific PDE inhibitor, a β-adrenergic agonist, a cAMP-dependent protein kinase activator, an $\alpha_1$-adrenergic antagonist, a superoxide anion ($O_2^-$) scavenger, an ATP-sensitive $K^+$ channel activator, an estrogen or estrogen mimetic, or a smooth muscle relaxant, are administered either in combination or sequentially to provide an enhanced therapeutic benefit. In particular, the use of an NO donor and a second agent from those provided above can provide fewer and less severe side effects than equally effective doses of NO donors, if used alone. More particularly, the use of an NO donor in combination with a second agent allows for decreased amounts of the NO donor to be used to achieve the same benefit relative to use alone, and provides significantly reduced occurrence and duration of headaches.

EXAMPLES

Example 1

This example illustrates the effect of cGMP mimetics, alone and in combination with a NO donor in a rat internal anal sphincter (IAS) relaxation model.

Male Sprague-Dawley rats (300–400 gm) were anesthetized with ketamine (90 mg/kg), xylazine (9 mg/kg) given intramuscularly and supplemented as needed with $\frac{1}{3}^{rd}$ dose. Rats were gently restrained on their backs on a heated surgical table (Harvard Apparatus) for the duration of the experiments. The diuretic effects of anesthesia was offset by rehydration with saline through an intraperitoneal implanted 24 gauge angiocatheter (VWR, San Francisco, Calif.). The constriction/relaxation measurement assembly included a Millar catheter/transducer (1.67 mm dia.) connected to a Digi-Med Low Pressure Analyzer (Micro-Med) accurate for pressure measurements between −50 and 150 mmHg. The data were integrated and converted to waveforms with the -Digi-Med System Integrator software. Blood pressure changes were monitored using an arterial catheter/transducer and a Digi-Med Blood Pressure Analyzer with the DMSI software. Respiratory changes were monitored using a mercury strain gauge/transducer, wrapped around the rib-cage of the rat, hooked up to a Digi-Med Analog Signal Analyzer along with the DMSI software. Drug delivery was accomplished through two Hamilton syringes with no dead space using PE 10 tubing adjacent to the catheter sensor. Drugs, typically were applied soon after stable baseline readings are recorded. Although unanesthetized restrained rats had been used in other studies, no differences have been observed in resting anal pressures after anesthesia; therefore, these studies were carried out with anesthetized rats to avoid undue distress to the animals.

Figure 2:
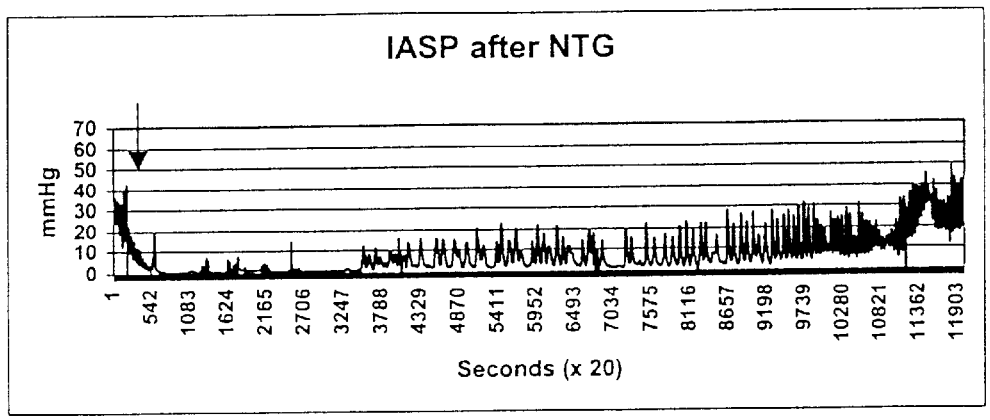
FIG. 2 illustrates the waveform pattern for IASP in a rat following administration of 20 µl of a 1% solution of nitroglycerin in propylene glycol.

Typical resting mean internal anal sphincter pressures (IASP) varyed between 30 and 60 mmHg in this model. The Millar catheter sensor allowed for accurate, isolated recordings of the IAS. FIG. 1 represents a typical waveform pattern for resting had minimal effect on IASP. The first 10 minutes after treatment with nitroglycerin is shown in FIG. 2.

Figure 3:
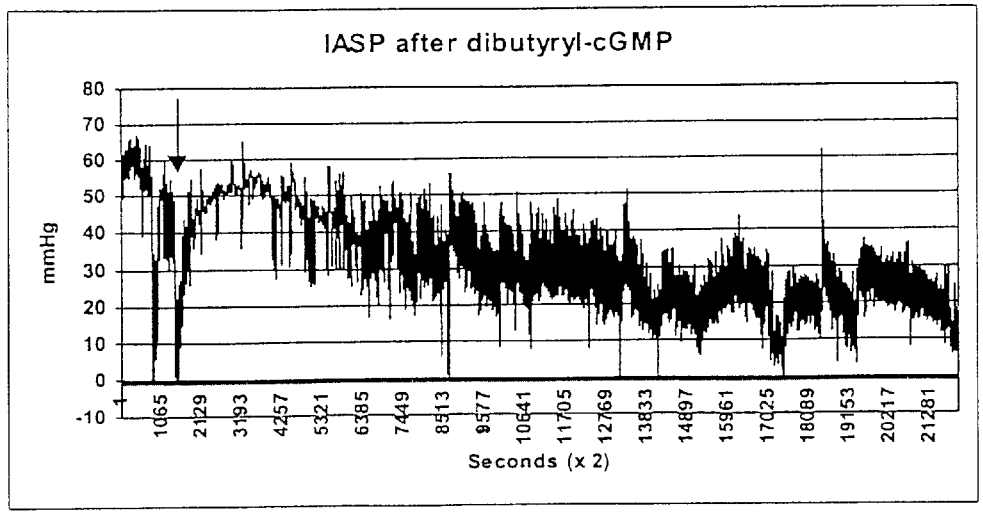
FIG. 3 illustrates the effect of a cGMP mimetic on internal anal sphincter pressure in a rat. The figure shows a waveform pattern for IASP for a rat following administration of 20 µl of a 10% solution of dibutyryl-cGMP in saline.

Using the same experimental protocol, the effect of a cGMP mimetic, dibutyryl-cGMP was studied. FIG. 3 shows that 20 μl of a 10% solution of dibutyryl-cGMP in saline applied to the anal canal reduced the mean IASP by 45% over 2.5 hours following treatment. The average IASP over the last hour prior to terminating the experiment had dropped 60%.

Figure 4:
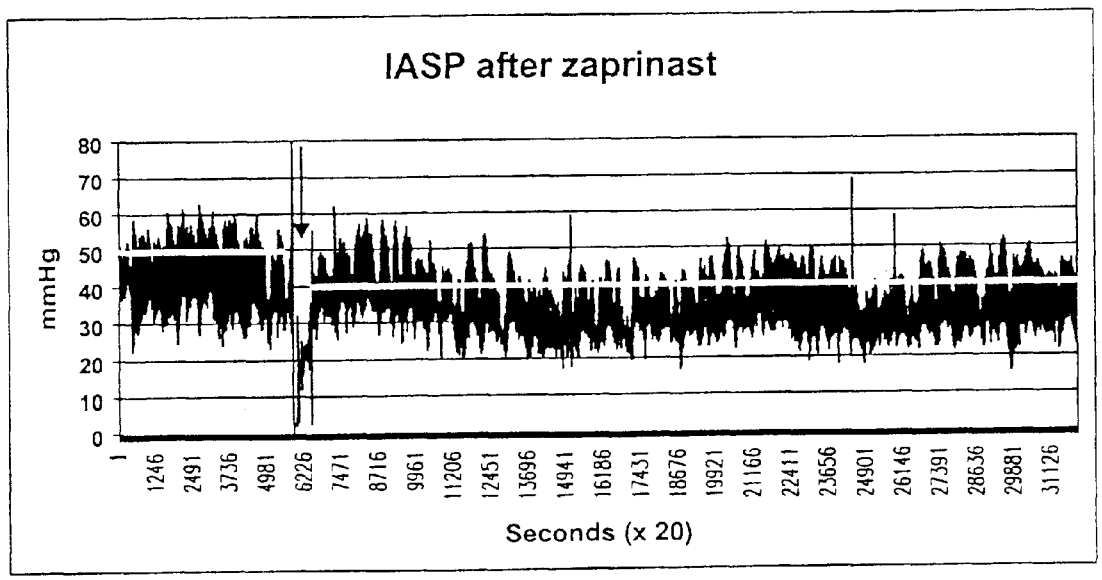
FIG. 4 illustrates the effect of a phosphodiesterase inhibitor on internal anal sphincter pressure in a rat. The figure shows a waveform pattern for IASP for a rat following administration of 20 µl of a 5% solution of zaprinast in 1-methyl-2 pyrrolidinone.

The IASP was still reduced 34% by the following morning indicating a potential long-term effect of the drug. A subsequent dose of 1% nitroglycerin dropped the IASP by 24% for 30 minutes and 71% for the first 10 minutes following treatment. After IASP returned to pre-treatment levels, a further dose of dibutyryl-cGMP was administered and found to lower IASP 15% over the ensuing 3 hours and 10 minutes (see FIG. 4).

These results support the effect of cGMP mimetics in relaxing anal sphincter muscle tone, and more importantly, suggest a potential benefit of using a combination of NO donor and cGMP mimetic due the quick onset of action of the NO donor and the more prolonged duration of relaxation produced by the cGMP mimetics.

Example 2

This example illustrates the effect of phosphodiesterase inhibitors in a rat internal anal sphincter relaxation model.

Using the same experimental protocol described above, an application of 20 μL of a 5% zaprinast solution in 1-methyl 2-pyrrolidinone reduced mean IASP by 21% over 32 minutes compared with vehicle treatment alone. The effect of phosphodieasterase inhibitors could be further enhanced by minimal concentrations of NO donors, such as nitroglycerin that produced a quicker onset and sustained sphincter relaxation without headache and other adverse reactions observed with high dose of NO donors alone.

Example 3

This example illustrates the effect of a potassium channel opener (minoxidil) in a rat internal anal sphincter constriction/relaxation model.

Figure 5:
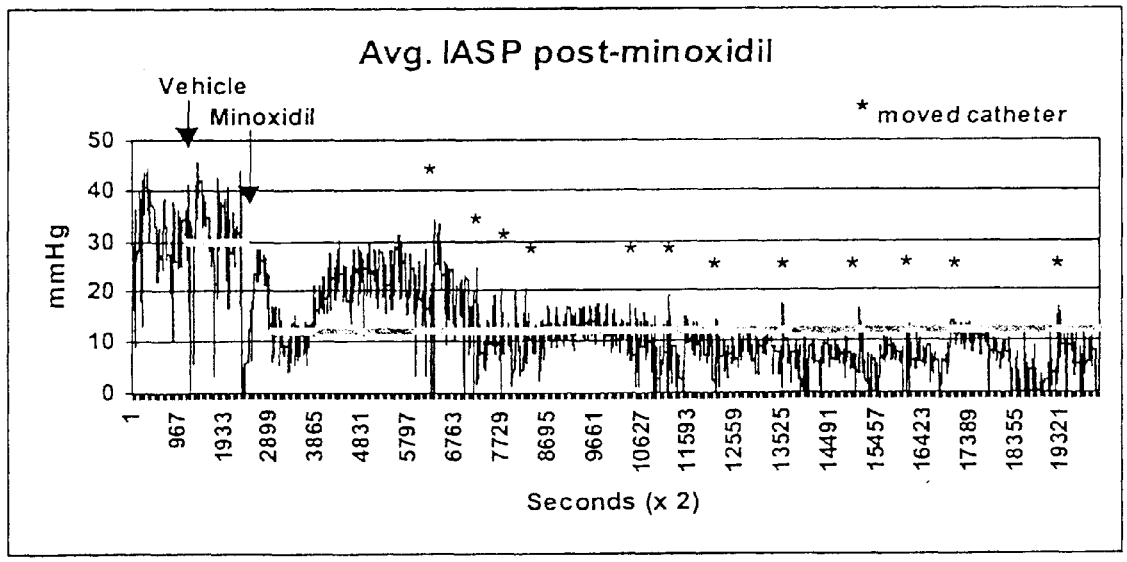
FIG. 5 illustrates the effect of a potassium channel opener on internal anal sphincter pressure in a rat. The figure shows a waveform pattern for IASP for a rat following administration of 20 µl of a 4% solution of minoxidil in 62.5% propylene glycol.

Following the same experimental protocol as described above, a single 20 μl dose of a 4% solution of minoxidil in 62.5% propylene glycol resulted in a 64% reduction of the IASP over 2.5 hours following treatment. The vehicle alone had little effect on IASP (see FIG. 5).

Example 4

This example illustrates a method for treating anal disorders in an individual using phosphodiesterase inhibitors and other agents to reduce pain associated with the disorders, including acute and chronic anal fissures.

Patients with severe anal pain and especially during and after bowel movement can be treated with the following therapies: zaprinast, zaprinast and nitroglycerin, minoxidil, nitroglycerin and cGMP mimetics, isoproterenol, or sildenafil, either one to three times daily or as required to effectively reduce anal rectal pain. Pain reduction (indicated by a reduction in the average pain and/or the defecation pain) will be evaluated and the time to pain reduction will also be evaluated. Therapy that is effective in relieving anal pain will eventually leads to effective resolution of these anal rectal disorders. Additionally, drugs that can effectively prevent recurrence of the diseases and yet cause minimal or no adverse reactions such as headache, dizzines, and hypotension will be of great therapeutic benefit.

Example 5

This example illustrates a method for treating anal disorders in an individual using phosphodiesterase inhibitors and other agents to promote healing in acute and chronic anal fissures.

Patients with anal fissures can be treated with the following therapies: zaprinast, zaprinast and nitroglycerin, minoxidil, nitroglycerin and cGMP mimetics, isoproterenol, or sildenafil, either one to three times daily or as required to effectively promote healing. Healing is indicated by improving re-epithelization of the observed fissure and can be evaluated along with the time needed to complete healing. Therapy that is effective in healing anal fissures eventually leads to complete resolution of these anal rectal disorders. Furthermore, drugs that can effectively prevent recurrence of the diseases and yet cause minimal or no adverse reactions such as headache will provide significant medical benefit.

Example 6

This example illustrates a method to reduce bleeding in patients with hemorrhoidal symptoms or diseases.

Patients with hemorrhoidal symptoms or diseases can be treated with the following therapies: zaprinast, zaprinast and nitroglycerin, minoxidil, nitroglycerin and cGMP mimetics, isoproterenol, or sildenafil, either one to three times daily or as required to effectively reduce bleeding and promote healing. Disease resolution indicated by reduction in bleeding and or pain can be evaluated along with the time to healing. Therapy that is effective in improving hemorrhoidal symptoms will eventually lead to complete resolution of these anal rectal disorders. Furthermore, drugs that can effectively prevent recurrence of the diseases while causing minimal or no adverse reactions such as headache are of significant medical benefit.

Example 7

A composition of a base gel comprising 1.0 gm of salbutamol, 0.6 gm of carbopol 1342 USP, 35.44 gm of propylene glycol, 15.16 gm of dehydrated ethanol USP, 15.16 gm of isopropyl alcohol USP, 2.5% oleic acid, triethanolamine HCl 1N to adjust the pH from 6.0 to 7.0, 0.05 gm of butylated hydroxytoluene NF, and 29.72 gm of purified water USP. Other concentrations of salbutamol can be added in the same gel base to achieve the therapeutically effective dose; this can also be achieved by adjusting the concentration of other β-agonists with gel base excipients such as oleic acid.

Example 8

One example of a topical composition comprises 0.05 to 1% sildenafil, 75% (w/w) white petrolatum USP, 4% (w/w)

paraffin wax USP/NF, lanolin 14% (w/w), 2% sorbitan sesquioleate NF, and 4% propylene glycol USP at the therapeutic effective dose to the anorectal area. Typically, the 50 mg to 600 mg of sildenafil ointment can be applied to the anorectal area in order to reduce the signs and/or symptoms associated with anorectal disorders, for example, anal fissure, anal ulcers, and hemorrhoidal diseases. The concentration of sildenafil, or other phosphodiesterase inhibitors can be varied by adjusting the ratio between the sildenafil with excipients facilitate either the attachment of sildenafil to the local tissue, or agents enhance absorption to the afflicted tissue.

Yet another example of a topical composition comprises nitroglycerin at 0.1% concentration and sildenafil at 0.1% concentration can be incorporated in the same ointment base as mentioned above. This composition can be applied topically from a metered dosing deviCe where a 50 mg to 1.5 gm dose of the composition is administered to the afflicted anorectal tissue to achieve the desired therapeutic effects.

Another therapeutic regimen is to provide patients afflicted with the anorectal disorders with both oral sildenafil tablets and topical nitroglycerin ointment. These two dosage forms can be used in combinations which provide the best efficacy and compliance among these patients.

Example 9

A composition of arninothylline topical spray composition comprises 0.1 to 5.0% (w/w) of aminothylline, acetylated lanolin alcohol, aloe vera, butane, cetyl acetate, hydrofluorocarbon, methyl paraben, PEG-8 laurate and polysorbate 80 in a 2 oz. pump spray bottle. The concentration of aminophylline or other non-specific phosphodiesterase inhibitor can vary between 0.5% to 5%. Other non-hydrofluorocarbon propellant can also be used instead of hydrofluorocarbon in the current composition. This composition can be sprayed directly onto the afflicted tissue once to four times daily to achieve the desired relief of signs and/or symptoms associated with anorectal disorders. This composition can also include menthol and benzocaine to provide the immediate local pain relief and soothing sensation whereas aminophylline provides the longer lasting relaxation of anal sphincter pressure.

Example 10

A base cream composition comprises 2 gm prazosin hydrochloride (2.0% w/w), 54.3 gm of purified water USP, 2 gm of Sepigel 305, 4.5 gm of Crodamol, 5.0 gm of glycerin, 6.0 gm sesame oil, 15.0 gm of white petrolatum USP, 2.0 gm of lanolin USP, 7.0 gm of 1,3-butylene glycol, 0.2 gm of methylparaben and 2.0 gm of silicon HL88.

A base cream can be prepared by first separate mixings of aqueous versus non-aqueous, i.e. oil phase, components of the cream. Once the aqueous phase containing the prazosin hydrochloride is well mixed, the melted oil phase is gently stirred into the aqueous phase to form a uniform cream base.

Example 11

Sildenafil, a specific inhibitor of type V phosphodiesterase, can be given orally via a tablet, parenterally or can be applied topically to patients diagnosed with anal fissures, either acute or chronic anal fissures, or other anorectal disorders. Sildenafil can be given one to three times daily for 8 weeks, especially in the case of patients afflicted with chronic anal fissure to cause the reduction of signs and symptoms associated with anorectal disorders.

For topical application, an approximate 50 mg to 900 mg dose of the cream measured by a metered dosing device, containing sildenafil, at the concentration from 0.02% to 5%, can be applied to the afflicted anorectal region using an applicator or by finger, one to four times daily to achieve the desirable therapeutic effects. Alternatively, the oral and topical treatment can be used in a defined regimen to achieve the best therapeutic effects.

Example 12

A phosphodiesterase inhibitor, for example aminophylline, can be given either orally via a tablet, parenterally or can be applied to patients diagnosed with anal fissures or other anorectal disorders, either acute or chronic anal fissures from a topical dosage form, e.g. a cream. For topical application, an approximate 50 mg to 900 mg of the cream measured by a metered dose device, can be applied to the afflicted anorectal region using an applicator or by finger, one to four times daily to achieve the desirable therapeutic effects.

Example 13

A $\beta$-adrenergic agonist, for example salbutamol, can be given from a suppository dosage form to patients diagnosed with anal fissures or other anorectal disorders, either acute or chronic anal fissures from a topical dosage form, e.g. a cream. For suppository application, an approximate 300 mg to 3 gm of the suppository unit can be applied to the afflicted anorectal region using an applicator or by finger, one to four times daily. Once the suppository melts in the anal cavity, the salbutamol released from the dosage form is available to achieve the desirable therapeutic effects.

Example 14

An $\alpha$-adrenergic antagonist, i.e. prazosin can be applied from a topical spray to patients diagnosed with hemorrhoidal disorders, alone or in combination with a local anesthetic, for example, lidocaine, or in combination with a mixed $\beta_2$- and $\beta_3$-adrenergic agonist, for example salbutamol, or in combination with a PDE IV inhibitor, for example, ariflo (SB207499), RP73401, CDP840, rolipram and LAS31025. Prazosin can be applied directly to the afflicted area with the propellant from the spray and can be used as needed to relieve the local pain and anal sphincter hypertonicity. Eventually, the application of prazosin leads to healing of the hemorrhoidal disorders.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating an anorectal disorder, and for controlling the pain associated therewith, the method comprising topically administering to the anorectal region of a subject in need of such treatment a therapeutically effective amount of a topical composition comprising an ATP-sensitive potassium channel opener in the amount of from about 0.01% to about 7.5%, wherein said therapeutically effective amount decreases hypertonicity of an anal sphincter muscle of the subject.

2. A method in accordance with claim 1, wherein said potassium channel opener is selected from the group consisting of minoxidil, minoxidil sulfate, pinacidil, diazoxide, levcromakalim, PCO400 and cromakalim.

3. A method in accordance with claim 2, wherein said potassium channel opener is minoxidil or minoxidil sulfate.

4. A method in accordance with claim 1, wherein said anorectal disorder is selected from the group consisting of an acute or chronic anal fissure, an internally or externally thrombosed hemorrhoid, a hemorrhoidal disease, a disorder associated with endoscopic hemorrhoidal ligation, levator spasm, constipation, and a disorder associated with hypertonicity or spasm of the anal sphincter muscle.

* * * * *